United States Patent
Liu et al.

(10) Patent No.: US 8,501,249 B2
(45) Date of Patent: Aug. 6, 2013

(54) GINGER EXTRACT FOR INHIBITING THE FAT-STORAGE FUNCTION OF ADIPOCYTES AND A MEDICATION THEREOF

(71) Applicant: Han Sheng Pharmtech, Inc., Pingtung (TW)

(72) Inventors: I-Min Liu, Kaohsiung (TW); Chia-Ju Chang, Kaohsiung (TW); Shorong-Shii Liou, Kaohsiung (TW)

(73) Assignee: Han Sheng Pharmtech, Inc., Pingtung (TW)

( * ) Notice: Subject to any disclaimer, the term of this patent is extended or adjusted under 35 U.S.C. 154(b) by 0 days.

(21) Appl. No.: 13/740,416

(22) Filed: Jan. 14, 2013

(65) Prior Publication Data

US 2013/0129846 A1 May 23, 2013

Related U.S. Application Data

(62) Division of application No. 13/178,596, filed on Jul. 8, 2011.

(51) Int. Cl.
*A61K 36/00* (2006.01)
*A61K 36/906* (2006.01)

(52) U.S. Cl.
USPC .......................................... 424/756; 424/725

(58) Field of Classification Search
None
See application file for complete search history.

*Primary Examiner* — Qiuwen Mi
(74) *Attorney, Agent, or Firm* — Alan Kamrath; Kamrath IP Lawfirm, P.A.

(57) ABSTRACT

In the present invention, a ginger extract for inhibiting the fat-store function of adipocytes and a medication thereof is disclosed, wherein the ginger extract is obtained form *Alpinia galanga* and *Zingiber zerumbet*. In the present invention, said ginger extract is further administrated to a target in need for inhibiting fat-storage function of adipocytes in the target.

8 Claims, 3 Drawing Sheets

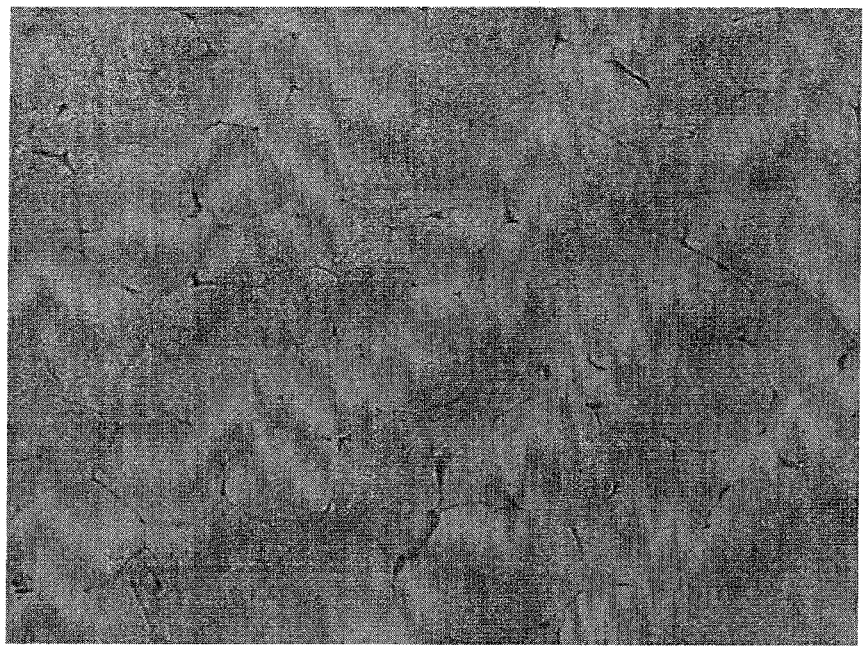
FIG. 2　50μm
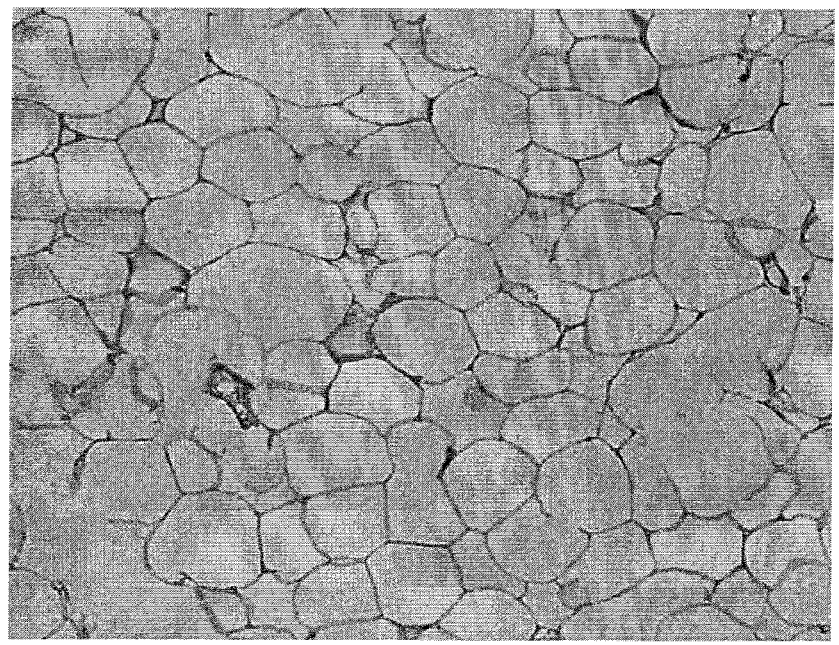
FIG. 3　50μm

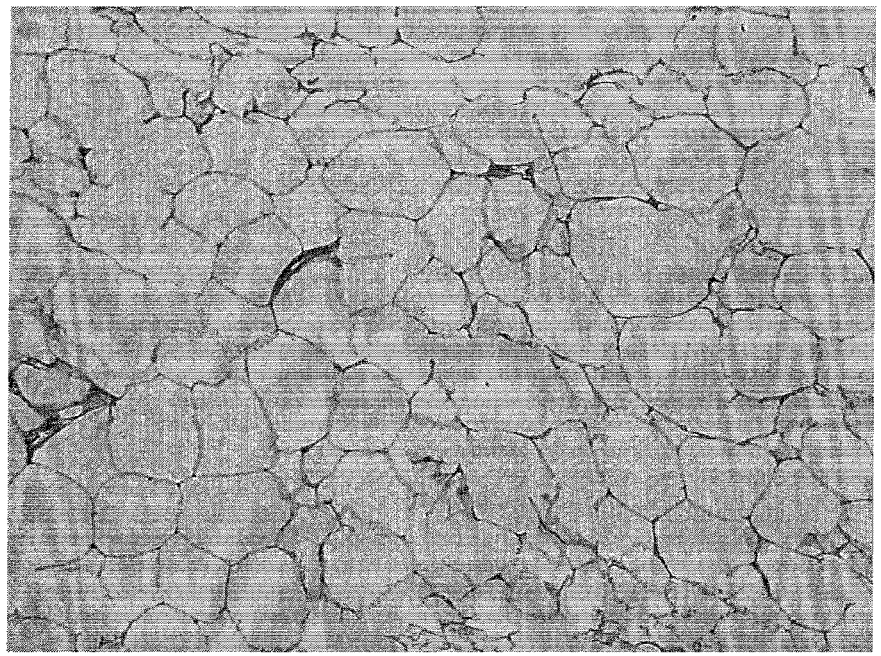
FIG. 4   50μm
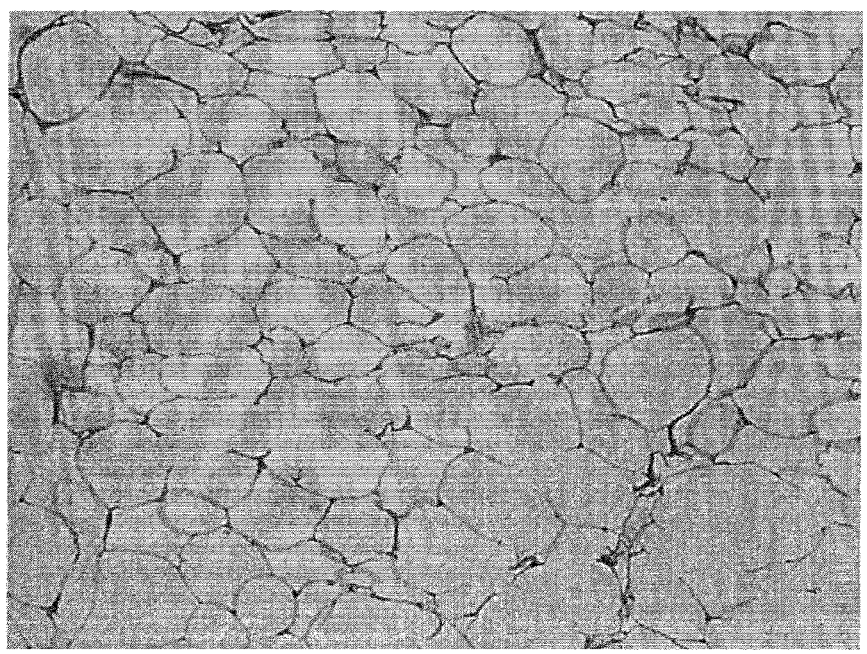
FIG. 5   50μm

GINGER EXTRACT FOR INHIBITING THE FAT-STORAGE FUNCTION OF ADIPOCYTES AND A MEDICATION THEREOF

This is a divisional application of U.S. patent application Ser. No. 13/178,596 filed on Jul. 8, 2011.

FIELD OF THE INVENTION

The present invention relates to a ginger extract and a therapeutic method by administrating the ginger extract and, more particularly, to a ginger extract which can inhibit the fat-storage function of adipocytes and a therapeutic method thereof.

DESCRIPTION OF THE RELATED ART

Adipose tissue refers to a loose connective tissue composed of adipocytes and is generally divided into two types, white adipose tissue and brown adipose tissue. The white adipose tissue mainly functions as a store of energy and the brown adipose tissue is for thermogenesis. In humans, adipose tissue is primary located in subcutaneous layers, in bone marrow and around internals, not only for reservation of liquid but also providing protective padding for organs.

In grown-up people, there are approximately thirty billion of adipocytes in bodies. The adipocytes play a key role in storage of triglyceride and energy-modulation. However, excess adipocytes in humans will lead to serious medical disorders, such as obesity.

Conventional anti-obesity medicine includes sibutramine, also known as meridian; orlistat, also known as xenical; chitonsan; and laxatives, for example magnesium oxide. Meridian will prolong the time effect of norepinephrine and serotonin, will accelerate the metabolism of the organism and finally will advance the consumption of fat. Xenical will inactivate lipase in the small intestine, to inhibit the lipolytic effects of the small intestine, as well as to absorb of fatty acid. Chitonsan will provide satiety to the user. Yet, laxatives will directly lead to diarrhea, eliminating excess fat from excretes in an enforced approach.

However, conventional anti-obesity medicine is less effective sometimes and is usually accompanied with plenty of side effects, such as being thirsty, insomnia, heat ache and constipation, which may result in inconvenience to people. Therefore, there is a pressing need of providing an anti-obesity method which is natural, effective and less risky, for the sake of providing a new strategy for losing weight in an easy and convenient process without any side effects.

SUMMARY OF THE INVENTION

An objective of this invention is to provide a ginger extract for inhibiting the fat-storage function of adipocytes, which can interfere with the fat-storage function of adipocytes to improve the issue of obesity.

Another objective of this invention is to provide a method of inhibiting the fat-storage function of adipocytes by administrating the ginger extract obtained from natural plants and capable of improving obesity due to the natural medical properties of ginger.

A ginger extract for inhibiting the fat-storage function of adipocytes is obtained by a process comprising the steps of drying, by providing roots or stems of *Alpinia galanga* and *Zingiber zerumbet*, followed by drying the roots or stems of *Alpinia galanga* and *Zingiber zerumbet* till the water content of the roots or stems of *Alpinia galanga* and *Zingiber zerumbet* is lower than 10%, to obtain dry *Alpinia galanga* and dry *Zingiber zerumbet*; extracting, by preparing a ginger component by mixing 25% to 75% of the dry *Alpinia galanga* and 25~75% of the dry *Zingiber zerumbet* and then extracting the ginger component with a solvent to obtain a liquid extract; and condensation, by condensing the liquid extract to obtain a ginger extract capable of inhibiting the fat-storage function of adipocytes.

A medication for inhibiting the fat-storage function of adipocytes, comprises a ginger extract; and a medical acceptable excipient.

A method of inhibiting fat-storage function of adipocytes, said method comprises administrating an effective amount of a ginger extract to a target in need thereof; wherein the ginger extract is obtained by a process comprising: providing roots or stems of *Alpinia galanga* and *Zingiber zerumbet*, followed by drying the roots or stems of *Alpinia galanga* and *Zingiber zerumbet* till water contents of the roots or stems of *Alpinia galanga* and *Zingiber zerumbet* being lower than 10%, to obtain a dry *Alpinia galanga* and a dry *Zingiber zerumbet*; preparing a ginger component by mixing the dry *Alpinia galanga* and the dry *Zingiber zerumbet* in a weight ratio of 1:3 to 3:1 and then extracting the ginger component with a solvent to obtain a liquid extract; and condensing the liquid extract.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 2 is a histosection datum of white adipose tissue in HD rats of groups D0-4;

FIG. 3 is a histosection datum of white adipose tissue in HD rats of groups D1-4;

FIG. 4 is a histosection datum of white adipose tissue in HD rats of groups D2-4; and FIG. 5 is a histosection datum of white adipose tissue in HD rats of groups D3-4.

Figure 1:
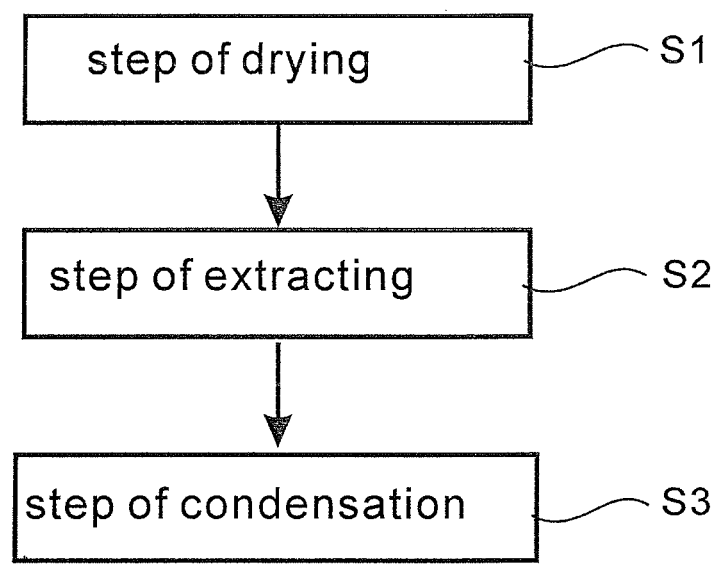
FIG. 1 is a diagram illustrating a manufacture method of a ginger extract in the present invention.

All figures are drawn for ease of explaining the basic teachings of the present invention only; the extensions of the figures with respect to number, position, relationship, and dimensions of the parts to form the preferred embodiments will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE PREFERRED EMBODIMENTS

Detailed Description of the Invention

With reference to FIG. 1, the present invention provides a ginger extract for inhibiting the fat-storage function of adipocytes, which is prepared by a manufacture method comprising a step of "drying S1," a step of "extracting S2," and a step of "condensation S3".

In the step of "drying S1," roots or stems of *Alpinia galanga* and *Zingiber zerumbe* are prepared and dried individually till the water content of the roots or stems of *Alpinia galanga* and *Zingiber zerumbe* decreases lower than 10%, in order to obtain dry *Alpinia galanga* and dry *Zingiber zerumbe*. More precisely, in the step of "drying S1," roots or stems of *Alpinia galanga* and *Zingiber zerumbe* are dried via, but not limited to, a lyophilization, spray drying, evaporation or heating drying.

*Alpinia galanga* of the present invention, also known as *Languas galanga*, is a kind of herbal medicine and has medical properties as an anti-inflammatory, for worm infestation and for hypersentivity reaction. Also, *Zingiber zerumbe* of the present invention, also known as the Shampoo Ginger, is regularly used as a food flavor or herbal medicine in various cuisines, and show medical properties in an anti-proliferation of cancer cell, and in a hypersentivity reaction.

In the step of "extracting S2," 25% to 75% of the dry *Alpinia galanga* and 25~75% of the dry *Zingiber zerumbet* are mixed with each other to obtain a ginger component. Then the ginger component is soaked and extracted by a solvent to obtain a liquid extract. The weight ratio between the ginger component and the solvent is 1:8 to 1:12. In the present invention, the solvent is but not limited to, water, methanol ethanol acetone, ethane, propane, butane or hexane. In the present embodiment, a ginger component is extracted by 95% ethanol under a process of sonication for 8 hours, for the sake of removing impurities in *Alpinia galanga* and *Zingiber zerumbet*, and obtaining the liquid extract of the present invention. With such performance, active substances in *Alpinia galanga* and *Zingiber zerumbet* are sufficient to be obtained from the liquid extract. Therefore the liquid extract of the present invention has potential to be put in use in the pharmaceutical industry, by manufacturing the liquid extract into medicament or health products for inhibiting the fat-storage function of adipocytes.

In the step of "condensation S3," the liquid extract is condensed to obtain a ginger extract for inhibiting the fat-storage function of adipocytes. As an example, the condensation of the liquid extract can be performed by evaporation or heating drying. In the present embodiment, the liquid extract is condensed via a process of evaporation, in order to remove solvent from the liquid extract and to obtain the ginger extract of the present invention. With such condensation, the ginger extract comprising a high concentration of active substances of *Alpinia galanga* and *Zingiber zerumbet* is successfully obtained, and which will be more significant in use of the pharmaceutical industries.

In the next paragraphs, the benefits of the ginger extract in anti-obesity are demonstrated by providing ginger components comprising dry *Alpinia galanga* and dry *Zingiber zerumbet* in various weight ratios, and carrying out a serial of trials with those ginger components in the present invention.

Referring to TABLE 1, seven ginger components comprising dry *Alpinia galanga* and dry *Zingiber zerumbet* in various weight ratios are prepared and extracted by 95% ethanol to obtain various extracts, and which includes groups (1) comprising dry *Alpinia galanga* only; (2) comprising dry *Zingiber zerumbet* only; (3) comprising dry *Alpinia galanga* and dry *Zingiber zerumbet* in a weight ratio of 1:1; (4) comprising dry *Alpinia galanga* and dry *Zingiber zerumbet* in a weight ratio of 2:1; (5) comprising dry *Alpinia galanga* and dry *Zingiber zerumbet* in a weight ratio of 3:1; (6) comprising dry *Alpinia galanga* and dry *Zingiber zerumbet* in a weight ratio of 1:2; and (7) comprising dry *Alpinia galanga* and dry *Zingiber zerumbet* in a weight ratio of 1:3. More precisely, the total weight of the ginger component of groups (1) to (7) is 6 kilograms, and the ginger component of groups (1) to (7) is extracted by 60 to 65 liters of 95% ethanol. In the present embodiment, extracts obtained from groups (1) to (7) are analyzed in trials of (A) toxicity, (B) anti fat-storage, and (C) animal.

TABLE 1

Ginger Components in Groups (1) to (7)

| Groups | Dry *Alpinia galanga* | Dry *Zingiber zerumbet* |
|---|---|---|
| (1) | — | 1 |
| (2) | 1 | — |
| (3) | 1 | 1 |
| (4) | 2 | 1 |
| (5) | 3 | 1 |
| (6) | 1 | 2 |
| (7) | 1 | 3 |

Trial (A): Toxicity

With reference to TABLE 2, the toxicity of the extracts of groups (1) to (7) is analyzed, by co-incubating a strain of adipocytes, named 3T3-L1 (with a sort code of BCRC 60159) and purchased from Bioresource Collection and Research Center of Food Industry Research and Development Institute in Taiwan, with the ginger extracts of groups (1) to (7) in various dosages, such as 0, 31.25, 62.5, 125, 250, 500 μg/ml, at 37° C., 5% $CO_2$, for 24 hours, and then analyzing the survival rate of the adipocytes 3T3-L1 in each groups via MTT assay. Precisely, $1 \times 10^4$ cells/ml of adipocytes 3T3-L1 are used in each group. In addition, the adipocytes 3T3-L1 is cultured at 37□, 5% $CO_2$, for 24 hours before the trial (A) of the present embodiment.

In an MTT assay of the present invention, the adipocytes 3T3-L1 of each group are co-incubated with an MTT reagent (3-(4,5-cimethlthiazol-2-yl)2,5,-diphenl tetrazolium bromide) for a period, and then the optical density (OD) of each group is analyzed by a spectrophotometer. With such arrangement, the tetrazolisum of the MTT (in yellow) will be transferred to formazan (in blue) under the reduction of dehdrogenase in live cells. Therefore, the survival rate of adipocytes 3T3-L1 in each group can be obtained by measuring the OD value the adipocytes 3T3-L1 of each group under 550 nm.

TABLE 2

Groups Assignment in Trial (A)

| Groups | Extracts | Dosage (μg/ml) |
|---|---|---|
| 1a | (1) | 0 |
| 1b | (1) | 31.25 |
| 1c | (1) | 62.25 |
| 1d | (1) | 125 |
| 1e | (1) | 250 |
| 1f | (2) | 500 |
| 2a | (2) | 0 |
| 2b | (2) | 31.25 |
| 2c | (2) | 62.25 |
| 2d | (2) | 125 |
| 2e | (2) | 250 |
| 2f | (2) | 500 |
| 3a | (3) | 0 |
| 3b | (3) | 31.25 |
| 3c | (3) | 62.25 |
| 3d | (3) | 125 |
| 3e | (3) | 250 |

TABLE 2-continued

Groups Assignment in Trial (A)

| Groups | Extracts | Dosage (μg/ml) |
|---|---|---|
| 3f | (3) | 500 |
| 4a | (4) | 0 |
| 4b | (4) | 31.25 |
| 4c | (4) | 62.25 |
| 4d | (4) | 125 |
| 4e | (4) | 250 |
| 4f | (4) | 500 |
| 5a | (5) | 0 |
| 5b | (5) | 31.25 |
| 5c | (5) | 62.25 |
| 5d | (5) | 125 |
| 5e | (6) | 250 |
| 5f | (6) | 500 |
| 6a | (6) | 0 |
| 6b | (6) | 31.25 |
| 6c | (6) | 62.25 |
| 6d | (6) | 125 |
| 6e | (6) | 250 |
| 6f | (6) | 500 |
| 7a | (7) | 0 |
| 7b | (7) | 31.25 |
| 7c | (7) | 62.25 |
| 7d | (7) | 125 |
| 7e | (7) | 250 |
| 7f | (7) | 500 |

According to TABLE 3, the survival rate of each group is summarized. It is noted that the survival of groups 1b to 1f, 2b to 2f, 3b to 3f, 4b to 4f, 5b to 5f, 6b to 6f and 7b to 7f are all higher than 90% in comparison with control groups individually, including 1a, 2a, 3a, 4a, 5a, 6a, and 7a, with the survival rate being defined as 100% in the present embodiment. Hence, it is suggested that the ginger extract will not damage cells.

TABLE 3

Survival Rate (%) of Groups 1a to 7f

| Groups | Survival Rate | Groups | Survival Rate | Groups | Survival Rate |
|---|---|---|---|---|---|
| 1a | 100 | 3c | 116.73 ± 1.14 | 5e | 101.25 ± 1.25 |
| 1b | 115.75 ± 1.24 | 3d | 113.71 ± 1.23 | 5f | 92.23 ± 1.23 |
| 1c | 111.69 ± 1.22 | 3e | 103.24 ± 1.12 | 6a | 100 |
| 1d | 113.35 ± 1.12 | 3f | 92.27 ± 1.15 | 6b | 98.76 ± 1.25 |
| 1e | 100.42 ± 1.12 | 4a | 100 | 6c | 99.27 ± 1.21 |
| 1f | 93.35 ± 1.23 | 4b | 104.88 ± 1.21 | 6d | 98.49 ± 1.25 |
| 2a | 100 | 4c | 112.44 ± 1.13 | 6e | 93.84 ± 1.27 |
| 2b | 114.26 ± 1.23 | 4d | 110.43 ± 1.16 | 6f | 92.32 ± 1.11 |
| 2c | 112.69 ± 1.12 | 4e | 106.02 ± 1.02 | 7a | 100 |
| 2d | 110.69 ± 1.21 | 4f | 91.35 ± 1.12 | 7b | 108.32 ± 1.09 |
| 2e | 101.35 ± 1.11 | 5a | 100 | 7c | 104.59 ± 1.15 |
| 2f | 93.58 ± 1.12 | 5b | 104.34 ± 1.25 | 7d | 105.93 ± 1.27 |
| 3a | 0 | 5c | 103.20 ± 1.21 | 7e | 102.36 ± 1.19 |
| 3b | 117.75 ± 1.12 | 5d | 102.20 ± 1.18 | 7f | 93.60 ± 1.18 |

Trial (B): Anti Fat-Storage

In the trial (B), the anti fat-storage function of the ginger extract in the present invention is demonstrated by using oil-red stain. With reference to TABLE 4, the adipocytes 3T3-L1 are prepared and cultured at a DMEM medium contained 10% bovine serum at first, followed by suspending the adipocytes 3T3-L1 with a trypsin-EDTA and counting the cell numbers of adipocytes. Next, $1 \times 10^6$ cells/ml of adipocytes 3T3-L1 in each group are collected and co-incubated with medium I at 37° C., 5% $CO_2$, for 2 days, then transferred to medium II and cultured for 3 days, and finally transferred to medium III for further culturing for 7 to 15 days. In the present embodiment, the adipocytes 3T3-L1 of each group are switched to fresh medium III every two days during the culturing of medium III.

TABLE 4

Formulas of Medium I, II, and III of the present invention

| | Contents | Concentration |
|---|---|---|
| I | Dulbecco's modified Eagle's medium | |
| | Calf serum | 10% |
| II | Dulbecco's modified Eagle's medium | |
| | Dexamethason | 1 μM |
| | 3-Isoytyl-1-methyl-xanthine | 0.5 mM |
| | insulin | 10 μM |
| | Indomethacin | 200 μM |
| | Fetal bovine serum | 10% |
| III | Dulbecco's modified Eagle's medium | |
| | insulin | 10 μM |
| | Fetal bovine serum | 10% |

In TABLE 5, it is shown that a control group, having untreated adipocytes 3T3-L1, and the adipocytes 3T3-L1 obtained from the above culturing are further cultured at 37° C., 5% $CO_2$, for 24 hours. Then the adipocytes 3T3-L1 obtained from the above culturing are randomly assigned into 42 groups and co-incubate with ginger extracts of groups (1) to (7) in a various dosage, such as 0, 31.25, 62.5, 125, 250, 500 μg/ml, at 37□, 5% $CO_2$, for 24 hours. Finally, adipoctes 3T3-L1 in the control group and groups (1A) to (7F) are analyzed via the oil-red stain.

TABLE 5

Groups Assignment in Trial (B)

| Groups | Extracts | Dosage (μg/ml) |
|---|---|---|
| 1A | (1) | 0 |
| 1B | (1) | 31.25 |
| 1C | (1) | 62.25 |
| 1D | (1) | 125 |
| 1E | (1) | 250 |
| 1F | (2) | 500 |
| 2A | (2) | 0 |
| 2B | (2) | 31.25 |
| 2C | (2) | 62.25 |
| 2D | (2) | 125 |
| 2E | (2) | 250 |
| 2F | (2) | 500 |
| 3A | (3) | 0 |
| 3B | (3) | 31.25 |
| 3C | (3) | 62.25 |
| 3D | (3) | 125 |
| 3E | (3) | 250 |
| 3F | (3) | 500 |
| 4A | (4) | 0 |
| 4B | (4) | 31.25 |
| 4C | (4) | 62.25 |
| 4D | (4) | 125 |
| 4E | (4) | 250 |
| 4F | (4) | 500 |
| 5A | (5) | 0 |
| 5B | (5) | 31.25 |
| 5C | (5) | 62.25 |
| 5D | (5) | 125 |
| 5E | (6) | 250 |
| 5F | (6) | 500 |
| 6A | (6) | 0 |
| 6B | (6) | 31.25 |
| 6C | (6) | 62.25 |
| 6D | (6) | 125 |
| 6E | (6) | 250 |
| 6F | (6) | 500 |
| 7A | (7) | 0 |

TABLE 5-continued

Groups Assignment in Trial (B)

| Groups | Extracts | Dosage (μg/ml) |
|---|---|---|
| 7B | (7) | 31.25 |
| 7C | (7) | 62.25 |
| 7D | (7) | 125 |
| 7E | (7) | 250 |
| 7F | (7) | 500 |

In the present embodiment, the oil-red stain is processed by removing the culturing medium from each group, washing with a PBS buffer, keeping at a fix solution, being a PBS buffer with 10% formalin, for 1 hour, removing the fix solution, and keeping at 0.2 ml of oil-red dye for another 1 hour. The oil-red dye is prepared by dissolving 50 ml oil-red in 10 ml isoacetone. The processed adipocytes 3T3-L1 of each group are analyzed by spectrophotometer at 510 nm.

In TABLE 6, the groups of (1A) to (7F) show significant performance in fat-storage in comparison with the untreated adipocytes 3T3-L1 (C). Furthermore, an anti fat-storage function is observed in groups (1B) to (1F), (2B) to (2F), (3B) to (3F), (4B) to (4F), (5B) to (5F), (6B) to (6F) and (7B) to (7F) in comparison with groups of (1A), (2A), (3A), (4A), (5A), (6A), and (7A) individually, especially in a dose-dependent manner. It is verified that the ginger extract of the present invention is sufficient to inhibit the fat-storage function of adipocytes, particularly to the ginger extract obtained from the ginger component having dry *Alpinia galanga* and dry *Zingiber zerumbe* in a weight ratio of 1:3.

TABLE 6

Fat-storage Rate (%) in Each Group

| Groups | Fat-storage Rate | Groups | Fat-storage Rate | Groups | Fat-storage Rate |
|---|---|---|---|---|---|
| 1A | 100 | 3C | 85.26 ± 2.14 | 5E | 80.18 ± 1.36 |
| 1B | 92.35 ± 1.21 | 3D | 81.43 ± 1.57 | 5F | 77.16 ± 1.72 |
| 1C | 90.23 ± 1.46 | 3E | 79.92 ± 1.64 | 6A | 100 |
| 1D | 88.65 ± 1.82 | 3F | 78.12 ± 1.38 | 6B | 80.26 ± 1.79 |
| 1E | 87.42 ± 2.13 | 4A | 100 | 6C | 78.31 ± 1.83 |
| 1F | 84.94 ± 1.57 | 4B | 86.21 ± 1.64 | 6D | 76.20 ± 2.28 |
| 2A | 100 | 4C | 83.25 ± 1.57 | 6E | 75.56 ± 2.17 |
| 2B | 91.47 ± 1.49 | 4D | 82.27 ± 1.35 | 6F | 73.22 ± 1.53 |
| 2C | 88.82 ± 1.53 | 4E | 80.98 ± 1.52 | 7A | 100 |
| 2D | 86.76 ± 1.25 | 4F | 78.09 ± 1.64 | 7B | 78.75 ± 1.48 |
| 2E | 84.21 ± 1.49 | 5A | 100 | 7C | 76.42 ± 1.62 |
| 2F | 80.83 ± 1.76 | 5B | 85.45 ± 1.39 | 7D | 74.59 ± 1.39 |
| 3A | 100 | 5C | 83.39 ± 1.43 | 7E | 72.09 ± 1.56 |
| 3B | 87.49 ± 1.72 | 5D | 81.32 ± 1.21 | 7F | 66.77 ± 1.42 |
| C (control) | 5.26 ± 0.18 | | | | |

Trial (C): Animal Test

In the present embodiment, male, around 200 to 250 grams and 8-weeks-old Wistar rats purchased from National Laboratory Animal Center in Taiwan are prepared, housed at a standard laboratory environment, such as keeping 25±1° C. and with 12 hour light/dark cycle, and fed with high fat diet (60 kcal %, TestDiet® Formula 58Y1) for 4 weeks. With such arrangement, high-fat diet-induced obesity rats (HD rats), gaining more than 40% weight, are obtained in the present invention, and will be used as an animal module in the trial (C) to further demonstrate the anti fat-storage function of the ginger extracts.

With reference to TABLE 7, the HD rats of the present invention are randomly assigned into 16 groups, including (D1), as a control and feeding with 1 ml water during the trial (C); (D2), feeding with ginger extract, containing dry *Alpinia galanga* and dry *Zingiber zerumbe* in a weight ratio of 1:3, in a dosage of 150 mg/per kilogram of weight daily during the trial (C); (D3) feeding with ginger extract, containing dry *Alpinia galanga* and dry *Zingiber zerumbe* in a weight ratio of 1:3, in a dosage of 300 mg/per kilogram of weight daily during the trial (C); and (D4); feeding with ginger extract, containing dry *Alpinia galanga* and dry *Zingiber zerumbe* in a weight ratio of 1:3, in a dosage of 600 mg/per kilogram of weight daily during the trial (C). In the present embodiment, the weights and the weight gain of the HD rats in each group are monitored at 0, 4, 8, and 12 weeks of the trial (C). Moreover, after the trial (C), white adipose tissues of the HD rats in each group are collected and analyzed by histological staining. In the present embodiment, the white adipose tissues of the HD rats are collected around the epididymis of the HD rats, followed by fixing with 10% formalin, embedding with paraffin, slicing and staining by hematoxylin and eosin stain.

TABLE 7

Groups Assignment in Trial (C)

| | | Weights | | | |
|---|---|---|---|---|---|
| Groups | Feeding | $0^{th}$ week | $4^{th}$ week | $8^{th}$ week | $12^{th}$ week |
| D1 | 1 ml water | 591.3 ± 3.7 | 656.9 ± 3.3 | 674.2 ± 5.9 | 687.3 ± 2.5 |
| D2 | 150 mg | 589.4 ± 4.2 | 612.6 ± 4.7$^a$ | 621.3 ± 4.1$^a$ | 625.1 ± 2.6$^a$ |
| D3 | 300 mg | 592.6 ± 5 | 583.6 ± 3.4$^a$ | 578.3 ± 3.8$^a$ | 571.2 |
| D4 | 600 mg | 587.5 ± 4.8 | 575.3 ± 3.5$^a$ | 564.3 ± 4.4$^a$ | 553.2 |

$^a$ $p < 0.05$

TABLE 8

Weight Gain of Rats in Trial (C)

| | Weight Gains | | | |
|---|---|---|---|---|
| Groups | $0^{th}$ week | $4^{th}$ week | $8^{th}$ week | $12^{th}$ week |
| D1 | — | 111.2% | 114.0% | 116.2% |
| D2 | — | 114.0% | 115.4% | 116.1% |
| D3 | — | 98.5% | 97.6% | 96.5% |
| D4 | — | 98.0% | 96.1% | 94.2% |

$^a$ $p < 0.05$

In TABLEs 7 and 8, the HD rats have a great amount of weight gain after having high-fat diet. However, feeding with ginger extract of the present invention, particularly in a dosage of 300 to 600 mg, will significantly reduce the weights of HD rats (see data in D2 and D3). It is proved that the ginger extract has benefits on the anti fat-storage of adipocytes. Additionally, in FIGS. 2 to 5, histosection photos of white adipose tissues of the HD rats in groups D1 to D4, being 200 times of magnification, are shown. It is suggested that, HD rats fed with the ginger extract of the present invention have smaller but more adipocytes in comparison with control rats (D1). In TABLE 10, numbers of adipocytes of the HD rats in group (D1) to (D4) are measured and recorded at the $12^{th}$ weeks in trial (C), and it is suggested that feeding with the ginger extract of the present invention will dramatically reduce the size of adipocytes in rats. As a result of reducing the size of adipocytes, the number of the adipocytes in a unit area in the histosection photo is increased. It is believed that the ginger extract of the present invention will significantly recover the symptoms caused by high-fat diets, such as gaining weight, and increasing of adipocyte in size.

TABLE 10

Numbers of Adipocyte in Groups (D1) to (D4) at the 12$^{th}$ weeks

| Groups | D1 | D2 | D3 | D4 |
|---|---|---|---|---|
| Numbers of Adipocyte (cell/pixel$^2$) | 79 ± 5.21 | 128 ± 6.42 | 152 ± 0.29 | 163 ± 4.63 |

It is suggested that the ginger extract of the present invention has potential to be applied to the pharmaceutical industry, being an active substance of medication or health products for inhibiting fat-storage function in adipose tissues. In the present invention, the ginger extract can be given to any target individually or combined with any acceptable excipient, for example carriers or other ingredients, and is capable of being further manufactured into any form of medicament, such as pill, capsule, powder, solution and pastil for easy and convenient delivery to targets. Preferably, the ginger extract of the present invention comprises dry *Alpinia galanga* and dry *Zingiber zerumbet* in a weight ratio of 1:3 to 3:1, particularly to 1:3, and is preferably delivered to a target in need once a day, with a dosage of 300 to 600 mg per kilogram of body weight and with a period of treatment lasting for 12 weeks for inhibiting fat-storage function of adipocytes of the target.

In summary, through the present invention, a ginger extract for inhibiting fat-storage function of adipose tissues is provide, by obtaining a ginger extract comprising dry *Alpinia galanga* and dry *Zingiber zerumbet* in a weight ratio of 1:3 to 3:1 via an easy, convenient and time-and-cost saving process. With the ginger extract of the present invention, medication or health products comprising the ginger extract are also easily obtained, have natural medical properties in anti-obesity, and will be easy to put to use in the pharmaceutical industries. Thus, by administrating the ginger extract of the present invention to a target in need will inhibit fat-storage function of adipocytes of the target, and then avoid obesity. In this way, the general public can successfully lose weight in an easier, healthier and more convenient process.

Thus, since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A method of inhibiting fat-storage function of adipocytes, said method comprising:
    administrating an effective amount of a ginger extract to a target in need thereof, wherein the ginger extract is obtained by a process comprising:
    providing roots or stems of *Alpinia galanga* and *Zingiber zerumbet*, followed by drying the roots or stems of *Alpinia galanga* and *Zingiber zerumbet* till water contents of the roots or stems of *Alpinia galanga* and *Zingiber zerumbet* being lower than 10%, to obtain a dry *Alpinia galanga* and a dry *Zingiber zerumbet*;
    preparing a ginger component by mixing the dry *Alpinia galanga* and the dry *Zingiber zerumbet* in a weight ratio of 1:3 to 3:1 and then extracting the ginger component with a solvent to obtain a liquid extract; and
    condensing the liquid extract.

2. The method of inhibiting the fat-storage function of adipocytes as defined in claim 1, wherein the solvent is selected from one of water, methanol, ethanol, acetone, ethane, propane, butane and hexane.

3. The method of inhibiting the fat-storage function of adipocytes as defined in claim 1, wherein the extracting comprises extracting the ginger component with the solvent in a weight ratio of 1:8 to 1:12.

4. The method of inhibiting the fat-storage function of adipocytes as defined in claim 1, wherein the extracting is processed via sonication.

5. The method of inhibiting the fat-storage function of adipocytes as defined in claim 1, wherein the drying is processed via lyophilization, spray drying, evaporation or heating drying.

6. The method of inhibiting the fat-storage function of adipocytes as defined in claim 1, wherein the condensing is processed via evaporation or heating drying.

7. The method of inhibiting the fat-storage function of adipocytes as defined in claim 1, wherein the administering comprises orally delivering the ginger extract to the target in need.

8. The method of inhibiting the fat-storage function of adipocytes as defined in claim 7, wherein orally delivering comprises orally delivering the ginger extract to the target in need at a dosage of 300 to 600 mg/per kilogram of body.

* * * * *